(12) United States Patent
Chang (10) Patent No.: US 9,758,575 B2
(45) Date of Patent: Sep. 12, 2017

(54) ANTIBODIES WHICH SPECIFICALLY BIND TO CANINE VASCULAR ENDOTHELIAL GROWTH FACTOR AND USES THEREOF

(71) Applicant: Yung Shin Pharmaceutical Industrial Co. Ltd., Taichung (TW)

(72) Inventor: Ming-Shi Chang, Tainan (TW)

(73) Assignee: Yung Shin Pharmaceutical Industrial Co. Ltd., Taichung (TW)

( * ) Notice: Subject to any disclaimer, the term of this patent is extended or adjusted under 35 U.S.C. 154(b) by 1 day.

(21) Appl. No.: 14/679,573

(22) Filed: Apr. 6, 2015

(65) Prior Publication Data

US 2016/0289313 A1    Oct. 6, 2016

(51) Int. Cl.
*A61K 39/395* (2006.01)
*C07K 16/22* (2006.01)
*A61K 45/06* (2006.01)
*A61K 39/00* (2006.01)

(52) U.S. Cl.
CPC .............. *C07K 16/22* (2013.01); *A61K 45/06* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| 7,517,524 | B2 * | 4/2009 | Nash | ...................... | C07K 14/52 |
|---|---|---|---|---|---|
| | | | | | 424/130.1 |
| 2014/0342405 | A1 | 11/2014 | Rosen et al. | | |
| 2015/0056183 | A9 * | 2/2015 | Gearing | ............. | C07K 16/2887 |
| | | | | | 424/133.1 |

FOREIGN PATENT DOCUMENTS

WO    WO 2012/153126 A1    11/2012

OTHER PUBLICATIONS

MacCallum et al. (J. Mol. Biol. 262:732-745 (1996)).*
de Pascalis et al. (Journal of Immunology 169, 3076-3084 (2002)).*
Vajdos et al. (J. Mol. Biol. 320, 415-428 (2002)).*
Holm et al (Mol. Immunol. 44: 1075-1084 (2007)).*
Wu et al. (J. Mol. Biol. 294, 151-162 (1999)).*
Gamlem et al., Canine neoplasia—introductory paper. APMIS Suppl. 2008;(125):5-18.
Keating, Bevacizumab: a review of its use in advanced cancer. Drugs. Oct. 2014;74(16):1891-925. doi: 10.1007/s40265-014-0302-9.
Macewen, Spontaneous tumors in dogs and cats: models for the study of cancer biology and treatment. Cancer Metastasis Rev. Sep. 1990;9(2):125-36.
Pavlidis et al., Role of bevacizumab in colorectal cancer growth and its adverse effects: a review. World J Gastroenterol. Aug. 21, 2013;19(31):5051-60. doi: 10.3748/wjg.v19.i31.5051.
Sleeckx et al., Canine mammary tumours, an overview. Reprod Domest Anim. Dec. 2011;46(6):1112-31. doi: 10.1111/j.1439-0531.2011.01816.x. Epub Jun. 6, 2011.
Tien et al., Downregulation of the KLF4 transcription factor inhibits the proliferation and migration of canine mammary tumor cells. Vet J. Aug. 2015;205(2):244-53. doi: 10.1016/j.tvjl.2014.12.031. Epub Jan. 5, 2015.
Trevisan et al., Antiangiogenic therapy of brain tumors: the role of bevacizumab. Neurol Sci. Apr. 2014;35(4):507-14. doi: 10.1007/s10072-014-1627-6. Epub Jan. 18, 2014.
Vail et al., Spontaneously occurring tumors of companion animals as models for human cancer. Cancer Invest. 2000;18(8):781-92.
Borgatti et al., Binding of VEGF-A to canine cancer cells with preferential expression of VEGFR1. Veterinary World. Jan. 2014;7(1):1-6.
Moschetta et al., Prognostic value of vascular endothelial growth factor and hypoxia-inducible factor 1α in canine malignant mammary tumors. Oncol Rep. May 2015;33(5):2345-53. doi: 10.3892/or.2015.3856. Epub Mar. 16, 2015.
Restucci et al., Expression of vascular endothelial growth factor in canine mammary tumors. Vet Pathol. Jul. 2002;39(4):488-93.

* cited by examiner

*Primary Examiner* — Christine J Saoud
(74) *Attorney, Agent, or Firm* — Wolf, Greenfield & Sacks, P.C.

(57) ABSTRACT

Disclosed herein are antibodies capable of inhibiting canine vascular endothelial growth factor and uses thereof in treating a canine angiogenesis-related disorder such as a proliferative disease.

15 Claims, 3 Drawing Sheets

```
                         SEQUENCE LISTING

<160> NUMBER OF SEQ ID NOS: 10

<210> SEQ ID NO 1
<211> LENGTH: 1389
<212> TYPE: DNA
<213> ORGANISM: Artificial Sequence
<220> FEATURE:
<223> OTHER INFORMATION: Synthetic Polynucleotide

<400> SEQUENCE: 1
atggaatgga cctgggtctt tctcttcctc ctgtcagtaa ctgcaggtgt ccactcccag      60
gttcagctgc agcagtctgg agctgagctg atgaagcctg gggcctcagt gaaaatatcc     120
tgcaaggcta ctggctacac attcagtagc tactggatag agtgggtaaa gcagaggcct     180
ggacatggcc ttgagtggat tggagagatt tttcctggag gtggtgatcc taaatacaat     240
gagaatttca agggcaaggc cacattcact acagatgcat cctccaacac agcctacatg     300
caactcagca gcctgacatc tgaggactct gccgtctatt actgtgcaag aggaaccttc     360
gggttctatg ctatggacta ctggggtcaa ggaacctcag tcaccgtctc ctcagccaaa     420
acgacacccc catctgtcta tccactggcc cctggatctg ctgcccaaac taactccatg     480
gtgaccctgg gatgcctggt caagggctat ttccctgagc cagtgacagt gacctggaac     540
```

```
tctggatccc tgtccagcgg tgtgcacacc ttcccagctg tcctgcagtc tgacctctac    600
actctgagca gctcagtgac tgtcccctcc agcacctggc ccagcgagac cgtcacctgc    660
aacgttgccc accggccag cagcaccaag gtggacaaga aaattgtgcc cagggattgt     720
ggttgtaagc cttgcatatg tacagtccca gaagtatcat ctgtcttcat cttcccccca    780
aagcccaagg atgtgctcac cattactctg actcctaagg tcacgtgtgt tgtggtagac    840
atcagcaagg atgatcccga ggtccagttc agctggtttg tagatgatgt ggaggtgcac    900
acagctcaga cgcaaccccg ggaggagcag ttcaacagca ctttccgctc agtcagtgaa    960
cttcccatca tgcaccagga ctggctcaat ggcaaggagt tcaaatgcag ggtcaacagt   1020
gcagctttcc ctgcccccat cgagaaaacc atctccaaaa ccaaaggcag accgaaggct   1080
ccacaggtgt acaccattcc acctcccaag gagcagatgg ccaaggataa agtcagtctg   1140
acctgcatga taacagactt cttccctgaa gacattactg tggagtggca gtggaatggg   1200
cagccagcgg agaactacaa gaacactcag cccatcatgg acacagatgg ctcttacttc   1260
gtctacagca agctcaatgt gcagaagagc aactgggagg caggaaatac tttcacctgc   1320
tctgtgttac atgagggcct gcacaaccac catactgaga agagcctctc ccactctcct   1380
ggtaaatga                                                          1389
```

<210> SEQ ID NO 2  
<211> LENGTH: 462  
<212> TYPE: PRT  
<213> ORGANISM: Artificial Sequence  
<220> FEATURE:  
<223> OTHER INFORMATION: Synthetic Polypeptide

<400> SEQUENCE: 2

```
Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Ile Ser Cys Lys Ala Thr Gly Tyr Thr Phe
        35                  40                  45

Ser Ser Tyr Trp Ile Glu Trp Val Lys Gln Arg Pro Gly His Gly Leu
    50                  55                  60

Glu Trp Ile Gly Glu Ile Phe Pro Gly Gly Asp Pro Lys Tyr Asn
65                  70                  75                  80

Glu Asn Phe Lys Gly Lys Ala Thr Phe Thr Thr Asp Ala Ser Ser Asn
                85                  90                  95

Thr Ala Tyr Met Gln Leu Ser Ser Leu Thr Ser Glu Asp Ser Ala Val
            100                 105                 110

Tyr Tyr Cys Ala Arg Gly Thr Phe Gly Phe Tyr Ala Met Asp Tyr Trp
        115                 120                 125

Gly Gln Gly Thr Ser Val Thr Val Ser Ser Ala Lys Thr Thr Pro Pro
    130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205
```

```
Pro Ser Ser Thr Trp Pro Ser Glu Thr Val Thr Cys Asn Val Ala His
    210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro
            260                 265                 270

Lys Val Thr Cys Val Val Val Asp Ile Ser Lys Asp Asp Pro Glu Val
        275                 280                 285

Gln Phe Ser Trp Phe Val Asp Asp Val Glu Val His Thr Ala Gln Thr
    290                 295                 300

Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
                325                 330                 335

Arg Val Asn Ser Ala Ala Phe Pro Ala Pro Ile Glu Lys Thr Ile Ser
            340                 345                 350

Lys Thr Lys Gly Arg Pro Lys Ala Pro Gln Val Tyr Thr Ile Pro Pro
        355                 360                 365

Pro Lys Glu Gln Met Ala Lys Asp Lys Val Ser Leu Thr Cys Met Ile
    370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asp Thr Asp
                405                 410                 415

Gly Ser Tyr Phe Val Tyr Ser Lys Leu Asn Val Gln Lys Ser Asn Trp
            420                 425                 430

Glu Ala Gly Asn Thr Phe Thr Cys Ser Val Leu His Glu Gly Leu His
        435                 440                 445

Asn His His Thr Glu Lys Ser Leu Ser His Ser Pro Gly Lys
    450                 455                 460

<210> SEQ ID NO 3
<211> LENGTH: 717
<212> TYPE: DNA
<213> ORGANISM: Artificial Sequence
<220> FEATURE:
<223> OTHER INFORMATION: Synthetic Polynucleotide

<400> SEQUENCE: 3
atgaagttgc ctgttaggct gttggtgctg atgttctgga ttcctgcttc cagcagtgat      60
gctgtgatga cccaaactcc actctccctg cctgtcagtc ttggagatca agtctccatc     120
tcttgcaggt ctagtcagag ccttgaaaac agtaatggaa acacctattt gaactggtac     180
ctccagaaac aggccagtc tccacagctc ctgatctaca gggtttccaa ccgattttct     240
ggggtcctag acaggttcag tggtagtgga tcagggacag atttcacact gaaaatcagc     300
agagtggagg ctgaggattt gggagtttat ttctgcctcc aagttacaca tgtcccctac     360
acgttcggag gggggaccaa gctggaaata aaacggctg atgctgcacc aactgtatcc     420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag gacagcaaag acagcaccta cagcatgagc     600
```

```
agcaccctca cgttgaccaa ggacgagtat gaacgacata acagctatac ctgtgaggcc    660
actcacaaga catcaacttc acccattgtc aagagcttca acaggaatga gtgttag       717
```

<210> SEQ ID NO 4
<211> LENGTH: 238
<212> TYPE: PRT
<213> ORGANISM: Artificial Sequence
<220> FEATURE:
<223> OTHER INFORMATION: Synthetic Polypeptide

<400> SEQUENCE: 4

```
Met Lys Leu Pro Val Arg Leu Leu Val Leu Met Phe Trp Ile Pro Ala
1               5                   10                  15

Ser Ser Ser Asp Ala Val Met Thr Gln Thr Pro Leu Ser Leu Pro Val
            20                  25                  30

Ser Leu Gly Asp Gln Val Ser Ile Ser Cys Arg Ser Ser Gln Ser Leu
        35                  40                  45

Glu Asn Ser Asn Gly Asn Thr Tyr Leu Asn Trp Tyr Leu Gln Lys Pro
    50                  55                  60

Gly Gln Ser Pro Gln Leu Leu Ile Tyr Arg Val Ser Asn Arg Phe Ser
65                  70                  75                  80

Gly Val Leu Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Leu Gln Val Thr His Val Pro Tyr Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```

<210> SEQ ID NO 5
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 5

```
Gly Tyr Thr Phe Ser Ser Tyr Trp Ile Glu
1               5                   10
```

<210> SEQ ID NO 6
<211> LENGTH: 17
<212> TYPE: PRT
<213> ORGANISM: Artificial Sequence
<220> FEATURE:
<223> OTHER INFORMATION: Synthetic Polypeptide

```
<400> SEQUENCE: 6

Glu Ile Phe Pro Gly Gly Gly Asp Pro Lys Tyr Asn Glu Asn Phe Lys
1               5                   10                  15

Gly

<210> SEQ ID NO 7
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 7

Gly Thr Phe Gly Phe Tyr Ala Met Asp Tyr
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 8

Arg Ser Ser Gln Ser Leu Glu Asn Ser Asn Gly Asn Thr Tyr Leu Asn
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 9

Arg Val Ser Asn Arg Phe Ser
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 10

Leu Gln Val Thr His Val Pro Tyr
1               5
```

ANTIBODIES WHICH SPECIFICALLY BIND TO CANINE VASCULAR ENDOTHELIAL GROWTH FACTOR AND USES THEREOF

BACKGROUND OF THE INVENTION

Vascular endothelial growth factor (VEGF) is involved in angiogenesis. Inhibition of VEGF influences this process and may restrict tumor growth and metastatic ability. Bevacizumab (AVASTIN®) is a recombinant humanized IgG1 monoclonal antibody, which binds to human VEGF-A and prevents its interaction with VEGF tyrosine kinase, thereby inducing blockage of VEGF-mediated angiogenesis.

Cancer is the leading cause of canine death. In necropsy (autopsy) of 2000 dogs, 23% of all dogs, regardless of age, and 45% of dogs 10 years of age or older attributed the cause of death as cancer. Estimates of age-adjusted overall cancer incidence rates per 100,000 animals per year at risk range from 381 for dogs. These are incidence rates comparable with rate of cancer in human beings (Vail et al., 2000).

SUMMARY OF THE INVENTION

The present disclosure is based, at least in part, the development of an anti-canine VEGF antibody which showed in vivo activities in blocking angiogenesis and reducing cancer cell growth and tumor volume.

Accordingly, one aspect of the present disclosure features an isolated antibody (non-naturally occurring antibody) that binds the same epitope in a canine vascular endothelial growth factor (VEGF) as antibody mAb 57C or competes for binding to the canine VEGF with antibody mAb 57C. The antibody may be a full length antibody or an antigen-binding fragment thereof. Alternatively or in addition, the antibody may be a canine antibody or a caninized antibody.

In some embodiments, the antibody may comprise:
a heavy chain that includes a heavy chain complementarity determining region 1 (HC CDR1) set forth as SEQ ID NO: 5, a heavy chain complementarity determining region 2 (HC CDR2) set forth as SEQ ID NO: 6, and a heavy chain complementarity determining region 3 (HC CDR3) set forth as SEQ ID NO: 7, and/or
a light chain that includes a light chain complementarity determining region 1 (LC CDR1) set forth as SEQ ID NO: 8, a light chain complementarity determining region 2 (LC CDR2) set forth as SEQ ID NO: 9, and a light chain complementarity determining region 3 (LC CDR3) set forth as SEQ ID NO: 10.

In some examples, the antibody may comprise a heavy chain variable region that comprises the amino acid sequence of SEQ ID NO: 2; and/or a light chain variable region that comprises the amino acid sequence of SEQ ID NO: 4.

In another aspect, the present disclosure features a nucleic acid or a set of nucleic acids that collectively encodes any of the anti-canine VEGF antibodies as described herein. Such a nucleic acid or nucleic acid set may be contained in a vector or a set of vectors, which can be an expression vector(s).

Further, the present disclosure provides a pharmaceutical composition comprising any of the anti-canine VEGF antibodies or any of the nucleic acid/nucleic acid set as described herein, and a pharmaceutically acceptable carrier (suitable for use in canine subjects).

The present disclosure also provides a method for treating an angiogenesis-related disease in a canine subject, comprising administering to a canine subject in need thereof an effective amount of any of the anti-canine VEGF antibodies described herein, or an effective amount of the nucleic acid/nucleic acid set that encodes the antibody. The method may further comprise administering to the canine subject an additional therapeutic agent for treating the target angiogenesis-related disease, for example, another chemotherapeutic agent for treating a canine cancer.

The canine subject that needs the treatment may be a dog having, is suspected of having, or at risk of having an angiogenesis-related disease. Exemplary angiogenesis-related diseases include, but are not limited to, a proliferative disease, macular degeneration, age-related macular degeneration, diabetic retinopathy, retinal detachment, glaucoma, pterygium of the conjunctiva and cornea, neuomyelitis optica, corneal neovascularization, neoplastic meningitis, myelofibrosis, radiation necrosis, and keloid. In some embodiments, the angiogenesis-related disease is a cancer (e.g., a solid tumor), which can be glioblastoma, sarcoma, hepatocellular carcinoma, inflammatory breast carcinoma, pancreatic cancer, metastatic melanoma, ovarian cancer, high-risk neuroblastoma, esophageal cancer, gastric cancer, metastatic head tumor, metastatic neck tumor, cervical cancer, peritoneal cancer, and squamous cell carcinoma.

Also within the scope of the present disclosure are (i) pharmaceutical compositions for use in treating any of the canine angiogenesis-related diseases as described herein, wherein the pharmaceutical composition comprises any of the anti-canine VEGF antibodies or the encoding nucleic acid/nucleic acid set as described herein and a pharmaceutically acceptable carrier; and (ii) uses of any of the antibodies or encoding nucleic acid(s) in manufacturing a medicament for use in treating the target canine angiogenesis-related disorders.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to the drawings in combination with the detailed description of specific embodiments presented herein.

FIGS. 1A-1C include diagrams showing administration of the anti-dVEGF mAb 57C reduced tumor growth in vivo.

FIGS. 2A-2C include diagrams showing the administration of the anti-VEGF mAb 57C reduced tumor growth in vivo.

FIGS. 3A-3C include diagrams showing the administration of the anti-VEGF mAb 57C reduced tumor growth in vivo.

DETAILED DESCRIPTION OF THE INVENTION

Canines develop angiogenesis-related diseases, such as cancer, with similar histopathologic and biologic behavior as such diseases in humans. Metastasis of canine cancers is frequent, and the effectiveness of chemotherapy and radiation has been limited. Canine malignant mammary tumors are fairly common in middle-aged animals and have a metastatic pattern similar to of mammary tumors in women. Canine mammary tumors (CMTs) are the most common neoplasm in female canines, and over 50% of CMTs are diagnosed as malignant (Tien et al., 2015). Although the prevalence of these tumors decreases in geographic regions where preventive ovariectomy is performed, it remains an important disease entity in veterinary medicine. Moreover, treatment options are limited in comparison with human breast cancer.

The present invention is based on the development of an antibody that binds canine vascular endothelial growth factor (VEGF), which reduced angiogenesis and exhibited in vivo anti-cancer activity. Accordingly, the methods disclosed herein provide treatment for canine subjects having or at risk of having angiogenesis-related diseases.

Anti-Canine VEGF Antibodies

Described herein are anti-canine antibody mAb 57C, an antigen-binding fragment thereof, as well as its functional equivalents and functional variants. Such antibodies binds to a canine VEGF, which may lead to reduction or prevention of the VEGF molecule from interacting with and/or activating VEGF receptor on a cell. Any of the antibodies described herein can be used for treating canine diseases associated with angiogenesis, such as cancer.

As used herein, the terms "antibody" and "immunoglobulin" may be used interchangeably and refer to full-length antibody molecules, e.g., IgG, IgA, IgD, IgE, and IgM, antigen binding fragments thereof, e.g., Fab, F(ab')2, Fab', and Fv, and genetically engineered antibody molecules, e.g., chimeric antibody, caninized antibody, scFv (single chain antibody), dAb (domain antibody; see Ward, et. al. (1989) Nature, 341: 544), and bi-specific antibody (e.g., capable of binding to VEGF and another molecule).

Any of the anti-canine VEGF antibodies described herein may be a genetically engineered antibody derived from a full-length antibody (e.g., chimeric, canalized, or single-chain) via, e.g., routine recombinant technology.

The anti-canine VEGF antibodies described herein can be either monoclonal or polyclonal. A "monoclonal antibody" refers to a homogenous antibody population and a "polyclonal antibody" refers to a heterogenous antibody population. These two terms do not limit the source of an antibody or the manner in which it is made.

The amino acid sequences and the encoding nucleotide sequences of the heavy and light chains of mAb 57C are provided below. The variable regions are indicated in boldface; the complementary determining regions (CDRs) are boldfaced and underlined; and the constant regions are in italics.

Heavy Chain Nucleotide Sequence
(SEQ ID NO: 1)
ATGGAATGGACCTGGGTCTTTCTCTTCCTCCTGTCAGTAACTGCAGG

TGTCCACTCCCAGGTTCAGCTGCAGCAGTCTGGAGCTGAGCTGATGA

AGCCTGGGGCCTCAGTGAAAATATCCTGCAAGGCTACT<u>GGCTACACA</u>

<u>TTCAGTAGCTACTGGATAGAGTGGG</u>TAAAGCAGAGGCCTGGACATGG
 CDR1

CCTTGAGTGGATTGGA<u>GAGATTTTTCCTGGAGGTGGTGATCCTAAAT</u>
                     CDR2

<u>ACAATGAGAATTTCAAGGGCAAGGCCACATTCACTACAGATGCATCC</u>

<u>TCCAACACAGCCTACATGCAACTCAGCAGCCTGACATCTGAGGACTC</u>

TGCCGTCTATTACTGTGCAAGA<u>GGAACCTTCGGGTTCTATGCTATGG</u>
                      CDR3

<u>ACTAC</u>TGGGGTCAAGGAACCTCAGTCACCGTCTCCTCA*GCCAAACG*

*ACACCCCCATCTGTCTATCCACTGGCCCCTGGATCTGCTGCCCAAAC*

*TAACTCCATGGTGACCCTGGGATGCCTGGTCAAGGGCTATTTCCCTG*

*AGCCAGTGACAGTGACCTGGAACTCTGGATCCCTGTCCAGCGGTGTG*

*CACACCTTCCCAGCTGTCCTGCAGTCTGACCTCTACACTCTGAGCAG*

*CTCAGTGACTGTCCCCTCCAGCACCTGGCCCAGCGAGACCGTCACCT*

*GCAACGTTGCCCACCCGGCCAGCAGCACCAAGGTGGACAAGAAAATT*

*GTGCCCAGGGATTGTGGTTGTAAGCCTTGCATATGTACAGTCCCAGA*

*AGTATCATCTGTCTTCATCTTCCCCCCAAAGCCCAAGGATGTGCTCA*

*CCATTACTCTGACTCCTAAGGTCACGTGTGTTGTGGTAGACATCAGC*

*AAGGATGATCCCGAGGTCCAGTTCAGCTGGTTTGTAGATGATGTGGA*

*GGTGCACACAGCTCAGACGCAACCCCGGGAGGAGCAGTTCAACAGCA*

*CTTTCCGCTCAGTCAGTGAACTTCCCATCATGCACCAGGACTGGCTC*

*AATGGCAAGGAGTTCAAATGCAGGGTCAACAGTGCAGCTTTCCCTGC*

*CCCCATCGAGAAAACCATCTCCAAAACCAAAGGCAGACCGAAGGCTC*

*CACAGGTGTACACCATTCCACCTCCCAAGGAGCAGATGGCCAAGGAT*

*AAAGTCAGTCTGACCTGCATGATAACAGACTTCTTCCCTGAAGACAT*

*TACTGTGGAGTGGCAGTGGAATGGGCAGCCAGCGGAGAACTACAAGA*

*ACACTCAGCCCATCATGGACACAGATGGCTCTTACTTCGTCTACAGC*

*AAGCTCAATGTGCAGAAGAGCAACTGGGAGGCAGGAAATACTTTCAC*

*CTGCTCTGTGTTACATGAGGGCCTGCACAACCACCATACTGAGAAGA*

*GCCTCTCCCACTCTCCTGGTAAATGA*

Heavy Chain Amino Acid Sequence
(SEQ ID NO: 2)
MEWTWVFLELLSVTAGVHSQVQLQQSGAELMKPGASVKISCKATGYT

FSSYWIEWVKQFPGHGLEWIGEIFPGGGDPKYNENFKGKATETTDAS
 CDR1              CDR2

SNTAYMQLSSLTSEDSAVYYCAR<u>GTFGFYAMDY</u>WGQGTSVTVSSAKT
                   CDR3

*TPPSVYPLAPGSAAQTNSMVTLGCLVKGYFPEPVTVTWNSGSLSSGV*

*HTFPAVLQSDLYTLSSSVTVPSSTWPSETVTCNVAHPASSTKVDKKI*

*VPRDCGCKPCICTVPEVSSVFIFPPKPKDVLTITLTPKVTCVVVDIS*

-continued

KDDPEVQFSWFVDDVEVHTAQTQPREEQFNSTFRSVSELPIMHQDWL

NGKEFKCRVNSAAFPAPIEKTISKTKGRPKAPQVYTIPPPKEQMAKD

KVSLTCMITDFFPEDITVEWQWNGQPAENYKNTQPIMDTDGSYFVYS

KLNVQKSNWEAGNTFTCSVLHEGLHNHHTEKSLSHSPGK

Light Chain Nucleotide Sequence
                                          (SEQ ID NO: 3)
ATGAAGTTGCCTGTTAGGCTGTTGGTGCTGATGTTCTGGATTCCTGC

TTCCAGCAGTGATGCTGTGATGACCCAAACTCCACTCTCCCTGCCTG

TCAGTCTTGGAGATCAAGTCTCCATCTCTTGC<u>AGGTCTAGTCAGAGC</u>

<u>CTTGAAAACAGTAATGGAAACACCTATTTGAAC</u>TGGTACCTCCAGAA
                    CDR1

ACCAGGCCAGTCTCCACAGCTCCTGATCTAC<u>AGGGTTTCCAACCGAT</u>
                                            CDR2

<u>TTTCTGGGGT</u>CCTAGACAGGTTCAGTGGTAGTGGATCAGGGACAGAT

TTCACACTGAAAATCAGCAGAGTGGAGGCTGAGGATTTGGGAGTTTA

TTTCTGC<u>CTCCAAGTTACACATGTCCCCTAC</u>ACGTTCGGAGGGGGA
               CDR3

CCAAGCTGGAAATAAAACGGGCTGATGCTGCACCAACTGTATCCATC

TTCCCACCATCCAGTGAGCAGTTAACATCTGGAGGTGCCTCAGTCGT

GTGCTTCTTGAACAACTTCTACCCCAAAGACATCAATGTCAAGTGGA

AGATTGATGGCAGTGAACGACAAAATGGCGTCCTGAACAGTTGGACT

GATCAGGACAGCAAAGACAGCACCTACAGCATGAGCAGCACCCTCAC

GTTGACCAAGGACGAGTATGAACGACATAACAGCTATACCTGTGAGG

CCACTCACAAGACATCAACTTCACCCATTGTCAAGAGCTTCAACAGG

AATGAGTGTTAG

Light Chain Amino Acid Sequence
                                          (SEQ ID NO: 4)
MKLPVRLLVLMFWIPASSSDAVMTQTPLSLPVSLGDQVSISCRSSQS

LENSNGNTYLNWYLQKPGQSPQLLIYRVSNRFSGVLDFFSGSGSGTD
     CDR1                         CDR2

FTLKISRVEAEDLGVYFCLQVTHVPYTFGGGTKLEIKRADAAPTVSI
                    CDR3

FPPSSEQLTSGGASVVCFLNNFYPKDINVKWKIDGSERQNGVLNSWT

DQDSKDSTYSMSSTLTLTKDEYERHNSYTCEATHKTSTSPIVKSFNR

NEC

Table 1 below lists the amino acid sequences of the heavy and light chain complementarity determining regions (CDRs) of antibody mAb 57C:

TABLE 1

| CDR Sequences of mAb 57C | | |
|---|---|---|
| CDR | Amino Acid Sequence | |
| Heavy chain | | |
| HC CDR1 | (CDR-H1) | GYTFSSYWIE (SEQ ID NO: 5) |
| HC CDR2 | (CDR-H2) | EIFPGGGDPKYNENFKG (SEQ ID NO: 6) |
| HC CDR3 | (CDR-H3) | GTFGFYAMDY (SEQ ID NO: 7) |

TABLE 1-continued

| CDR Sequences of mAb 57C | | |
|---|---|---|
| CDR | Amino Acid Sequence | |
| Light chain | | |
| LC CDR1 | (CDR-L1) | RSSQSLENSNGNTYLN (SEQ ID NO: 8) |
| LC CDR2 | (CDR-L2) | RVSNRFS (SEQ ID NO: 9) |
| LC CDR3 | (CDR-L3) | LQVTHVPY (SEQ ID NO: 10) |

In some embodiments, the antibody described herein comprises the same heavy chain complementarity determining region 1 (HC CDR1), complementarity determining region 2 (HC CDR2), complementarity determining region 3 (HC CDR3) as those of monoclonal antibody 57C. In some embodiments, the antibody herein has the same heavy chain variable region (VH) as that of anti-canine VEGF antibody 57C. In some embodiments, the antibody described herein comprises the same light chain complementarity determining region 1 (LC CDR1), complementarity determining region 2 (LC CDR2), complementarity determining region 3 (LC CDR3) as those of monoclonal antibody 57C. In some embodiments, the antibody herein has the same light chain variable region (VL) as that of anti-canine VEGF antibody 57C.

In some embodiments, the antibody used in the methods described herein is a functional equivalent of mAb 57C. Such a functional equivalent may be an antibody that binds to the same epitope of canine VEGF, and may exhibits at least 20% (e.g., 30%, 40%, 50%, 60%, 70%, 80%, 90%, or greater) of the activity of neutralizing a signaling pathway mediated by VEGF as relative to antibody 57C. Alternatively or in addition, such a functional equivalent of mAb 57C may exhibits at least 20% (e.g., 30%, 40%, 50%, 60%, 70%, 80%, 90%, or greater) of the activity of reducing cell proliferation mediated by VEGF as relative to antibody 57C.

An "epitope" of canine VEGF refers to the site on a canine VEGF (e.g., GenBank Accession No. NP_001003175, NP_001103972, or NP_001103971) that is bound by an antibody such as a Fab or full length antibody. Such a target site can be entirely composed of amino acid components, entirely composed of chemical modifications of amino acids of the protein (e.g., glycosyl moieties), or composed of combinations thereof. Overlapping epitopes include at least one common amino acid residue, glycosyl group, phosphate group, sulfate group, or other molecular feature.

A first binding antibody "binds to the same epitope" as a second binding antibody if the first binding antibody binds to the same site on a target compound that the second binding antibody binds, or binds to a site that overlaps (e.g., 50%, 60%, 70%, 80%, 90%, or 100% overlap, e.g., in terms of amino acid sequence or other molecular feature (e.g., glycosyl group, phosphate group, or sulfate group)) with the site that the second binding antibody binds. The specific epitope in the canine VEGF to which an antibody binds can be determined by routine technology.

Further, the functional equivalent of mAb 57C may be an antibody that competes against mAb 57C for binding to the target canine VEGF. A first binding antibody "competes for binding" with a second binding antibody if the binding of the first binding antibody to its epitope decreases (e.g., by 10%, 20%, 30%, 40%, 50%, 60%, 70%, 80%, 90%, 100%, or more) the amount of the second binding antibody that binds to its epitope. The competition can be direct (e.g., the first binding antibody binds to an epitope that is the same as, or overlaps with, the epitope bound by the second binding antibody), or indirect (e.g., the binding of the first binding antibody to its epitope causes a steric change in the target compound that decreases the ability of the second binding antibody to bind to its epitope). Whether an antibody competes against mAb 57C for binding to the target antigen can be determined by routine practice, e.g., competitive ELISA.

In some embodiments, the anti-canine VEGF antibody described herein is a functional variant of mAb 57C, which is an antibody that is both structurally and functional similar to mAb 57C. In some instances, a functional variant of antibody mAb 57C contains the same regions/residues responsible for antigen-binding as antibody mAb 57C, such as the same specificity-determining residues in the heavy chain and/or light chain CDRs or the whole CDRs. The regions/residues that are responsible for antigen-binding can be identified from amino acid sequences of the heavy chain/light chain sequences of antibody 57C (shown above) by methods known in the art. See, e.g., bioinf.org.uk/abs; Almagro, *J. Mol. Recognit.* 17:132-143 (2004); and Chothia et al., *J. Mol. Biol.* 227:799-817 (1987). In some examples, the anti-canine VEGF antibody described herein comprises the same heavy chain and light chain CDRs as mAb 57C. See Table 1 above.

In some examples, a functional variant of the anti-canine VEGF antibody 57C comprises a heavy chain that includes a HC CDR1, HC CDR2, and HC CDR3 at least 75% (e.g., 80%, 85%, 90%, 95%, or 98%) identical to the corresponding HC CDRs of antibody 57C, and a light chain that includes a LC CDR1, LC CDR2, and LC CDR3 at least 75% (e.g., 80%, 85%, 90%, 95%, or 98%) identical to the corresponding LC CDRs of antibody 57C.

Alternatively, the functional equivalent of the anti-canine VEGF antibody 57C comprises a HC variable region at least 75% (e.g., 80%, 85%, 90%, 95%, or 98%) identical to the HC variable region chain of antibody 57C and a LC variable region at least 75% (e.g., 80%, 85%, 90%, 95%, or 98%) identical to the LC variable region of antibody 57C.

The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In some embodiments, a functional variant of the anti-canine VEGF antibody 57C comprises a HC variable region that includes up to 5 (e.g., 1, 2, 3, 4, or 5) amino acid residue variations in the HC CDR regions (HC CDR1, CDR2, and/or CDR3) as compared to the HC CDRs of antibody 57C, and/or a LC variable region that includes up to 5 (e.g., 1, 2, 3, 4, or 5) amino acid residue variations in the LC CDR regions (LC CDR1, CDR2, and/or CDR3) as compared to the LC CDRs of antibody 57C.

In one example, the functional variant of mAb 57C is a caninized antibody. A caninized antibody contains a canine immunoglobulin (i.e., recipient antibody) in which regions/residues responsible for antigen binding (e.g., the complementarity determining regions, particularly the specificity-determining residues therein) are replaced with those from a non-canine immunoglobulin (i.e., donor antibody). Methods to identify regions/residues in the heavy and light chains of an antibody are well known in the art. See, e.g., Almagro, J. Mol. Recognit. 17:132-143 (2004); and Chothia et al., J. Mol. Biol. 227:799-817 (1987). In some instances, one or more residues inside a framework region of the recipient antibody are also replaced with those from the donor antibody. A caninized antibody may also contain residues from neither the recipient antibody nor the donor antibody. These residues are included to further refine and optimize antibody performance. Canine immunoglobulin genes are well known in the art. See, e.g., imgt.org/IMGTveterinary/#Dog.

In another example, the anti-canine VEGF antibody described herein is a chimeric antibody, which can include a heavy constant region and a light constant region from a canine antibody. A chimeric antibody has a variable region or part of variable region from a first species and a constant region from a second species. Typically, in these chimeric antibodies, the variable region of both light and heavy chains mimics the variable regions of antibodies derived from one species of mammals (e.g., a non-human mammal), while the constant portions are homologous to the sequences in antibodies derived from another (e.g., canine). In some embodiments, amino acid modifications can be made in the variable region and/or the constant region.

Methods of making various types of antibodies (e.g., monoclonal and polyclonal antibodies, antigen-binding fragments thereof, and genetically engineered antibodies), are well known in the art. See, for example, Harlow and Lane, (1988) Antibodies: A Laboratory Manual, Cold Spring Harbor Laboratory, New York.

In general, to produce antibodies against a protein (e.g., canine VEGF), the protein or a fragment thereof, optionally coupled to a carrier protein, such as KLH, can be mixed with an adjuvant, and injected into a host animal. Antibodies produced in the animal can then be purified by peptide affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, CpG, surface-active substances such as lysolecithin, pluronic polyols, polyanions, peptides, oil emulsions, keyhole limpet hemocyanin, and dinitrophenol. Useful adjuvants include BCG (bacille Calmette-Guerin) and *Corynebacterium parvum*.

Polyclonal antibodies are present in the sera of the immunized subjects. Monoclonal antibodies can be prepared using standard hybridoma technology (see, for example, Kohler et al. (1975) *Nature* 256, 495; Kohler et al. (1976) *Eur. J. Immunol.* 6, 511; Kohler et al. (1976) *Eur J Immunol* 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) *Nature* 256, 495 and U.S. Pat. No. 4,376,110; the B-cell hybridoma technique (Kosbor et al. (1983) *Immunol Today* 4, 72; Cole et al. (1983) *Proc. Natl. Acad. Sci. USA* 80, 2026, and the EBV hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies disclosed herein may be cultivated in vitro or in vivo. The ability to produce high titers of monoclonal antibodies in vivo makes it a particularly useful method of production.

Antigen-binding fragments of anti-canine VEGF antibodies antibody can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as caninized antibodies, chimeric antibodies, single-chain antibodies, and bi-specific antibodies, can be produced via conventional recombinant technology. Techniques developed for the production of "chimeric antibodies" can be used. See, e.g., Morrison et al. (1984) *Proc. Natl. Acad. Sci. USA* 81, 6851; Neuberger et al. (1984) *Nature* 312, 604; and Takeda et al. (1984) *Nature* 314:452.

Antibodies can also be caninized by methods known in the art. For example, a caninized antibody can be designed as follows. First, the variable regions of VH and VL of a parent non-canine antibody are subjected to three-dimensional molecular modeling analysis following methods known in the art (e.g., similar to methods for making humanized antibodies). See, e.g., Queen et al., *Proc. Natl. Acad. Sci. USA*, 86:10029-10033 (1989). Next, framework amino acid residues predicted to be important for the formation of the correct CDR structures are identified using the same molecular modeling analysis. In parallel, canine VH and VL chains having amino acid sequences that are homologous to those of the parent non-canine antibody are identified from any antibody gene database using the parent VH and VL sequences as search queries. Canine VH and VL acceptor genes are then selected. The CDR regions within the selected dog acceptor genes can be replaced with the CDR regions from the parent non-canine antibody or functional variants thereof. When necessary, residues within the framework regions of the parent chain that are predicted to be important in interacting with the CDR regions (see above description) can be used to substitute for the corresponding residues in the canine acceptor genes. Additional methods for caninization of antibodies are known in the art. See, e.g., WO2003060080, and WO2013184871, the relevant contents of each of which are incorporated by reference herein.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage scFv library and scFv clones specific to VEGF can be identified from the library following routine procedures. Positive clones can be subjected to further screening to identify those that bind VEGF, suppress VEGF receptor activity, and/or reduce cell proliferation.

After obtaining antibodies specific to the target antigen, their ability to neutralize the signaling pathway mediated by VEGF can be determined by a routine procedure. For example, the level of cell proliferation induced by VEGF is used as an indicator of VEGF receptor activity. In some embodiments, VEGF and/or VEGF receptor signaling may be assessed by any method known in the art, for example monitoring VEGF receptor phosphorylation, cell migration, cell proliferation, blood vessel formation, and/or tumor size. Antibodies that specifically binding to canine VEGF and suppress its activity (e.g., activation of VEGF receptor) are selected for use in the methods disclosed herein.

Use of Anti-Canine VEGF Antibodies

Also provided herein are methods for treating a canine disease associated with angiogenesis (e.g., cancer) using one or more of the anti-canine VEGF antibodies as described herein.

As used herein, the term "treating" refers to the application or administration of a composition including one or more active agents to a subject that has an angiogenic-related disease, a symptom of an angiogenic-related disease, or is at risk of having an angiogenic-related disease, with the purpose to cure, heal, alleviate, relieve, alter, remedy, ameliorate, improve, or affect the angiogenic-related disease, the symptom of an angiogenic-related disease, or risk of having an angiogenic-related disease.

In some embodiments, the anti-canine VEGF antibody described herein is administered to a subject in need of the treatment at an amount sufficient to reduce the level of the VEGF-mediated signaling by at least 20% (e.g., 30%, 40%, 50%, 60%, 70%, 80%, 90% or greater). In some embodiments, the anti-canine VEGF antibody described herein is administered to a subject in need of the treatment at an amount sufficient to reduce cell proliferation by at least 20% (e.g., 30%, 40%, 50%, 60%, 70%, 80%, 90% or greater). In some embodiments, the antibody is administered in an amount effective in reducing the number of cancer cells, reducing the size of a tumor, or preventing the growth of a tumor. In any of the embodiments described herein, the anti-canine VEGF antibody may be administered with another chemotherapeutic agent.

The antibodies described herein may be used to treat an angiogenesis-related disease in a canine subject. Non-limiting examples of angiogenesis-related disease include cancer, macular degeneration, age-related macular degeneration, diabetic retinopathy, retinal detachment, glaucoma, pterygium of the conjunctiva and cornea, neuomyelitis optica, corneal neovascularization, neoplastic meningitis, myelofibrosis, radiation necrosis, and keloid. In some embodiments, the angiogenesis-related canine disease is a proliferative disease such as a cancer (e.g., a solid tumor). Examples include, but are not limited to, glioblastoma, sarcoma, hepatocellular carcinoma, inflammatory breast carcinoma pancreatic cancer, metastatic melanoma, ovarian cancer, high-risk neuroblastoma, esophageal cancer, gastric cancer, metastatic head tumor, metastatic neck tumor, cervical cancer, peritoneal cancer, squamous cell carcinoma.

In some embodiments, the canine subject may be treated by a combination of any of the anti-canine VEGF antibody as described herein and an additional chemotherapeutic agent suitable for use in treating a canine cancer. The canine subject can be a dog having, suspected of having, or at risk for a cancer, e.g., those described herein or known in the art. In some embodiments, the chemotherapeutic agent is administered concomitantly with the anti-canine VEGF antibody. Examples of chemotherapeutic agents include, without limitation, Actinomycin, All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine. Additional chemotherapeutic agents will be known in the art See, e.g., PCT Publication No. 2005/012359.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Any of the anti-canine VEGF antibodies described herein can be formulated into a pharmaceutical composition, which further comprises one or more pharmaceutically acceptable carriers for use in dogs. In some embodiments, the anti-canine VEGF antibodies are formulated for administration to canine subjects. In some embodiments, the anti-canine VEGF antibodies are formulated for administration with another chemotherapeutic agent. "Acceptable" means that the carrier must be compatible with the active ingredient of the composition (and preferably, capable of stabilizing the active ingredient) and not deleterious to the canine subject to be treated. Suitable carriers include microcrystalline cellulose, mannitol, glucose, defatted milk powder, polyvinylpyrrolidone, and starch, or a combination thereof.

The pharmaceutically acceptable carriers, excipients, or stabilizers suitable for use in preparation of the just-noted pharmaceutical compositions can be in the form of lyophilized formulations or aqueous solutions as known in the art. They may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™ (polysorbate 20), PLURONICS™ (polyoxyalkylene ether) or polyethylene glycol (PEG).

The pharmaceutical compositions as described herein can be formulated for storage by mixing an antibody having the desired degree of purity with optional pharmaceutically acceptable carriers, excipients or stabilizers mentioned above. See, e.g., Remington: The Science and Practice of Pharmacy 20th Ed. (2000) Lippincott Williams and Wilkins, Ed. K. E. Hoover.

In some examples, the pharmaceutical compositions comprise liposomes encapsulating any of the antibodies described herein. Such liposomes can be prepared by methods known in the art. See, e.g., Epstein, et al., *Proc. Natl. Acad. Sci. USA* 82:3688 (1985); Hwang, et al., *Proc. Natl. Acad. Sci. USA* 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients (e.g., the anti-canine VEGF antibody) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

In other examples, the pharmaceutical compositions can be formulated in sustained-release form. Suitable examples of sustained-release formulations include semipermeable matrices of solid hydrophobic polymers containing the antibody, which matrices are in the form of shaped articles, e.g. films, or microcapsules. Examples of sustained-release matrices include polyesters, hydrogels (for example, poly (2-hydroxyethyl-methacrylate), or 'poly(v nylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can also be prepared in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. TWEEN™ 20, 40, 60, 80 or 85) and other sorbitans (e.g. SPAN™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as INTRALIPID™, LIPOSYN™, INFONUTROL™, LIPOFUNDIN™ and LIPIPHYSAN™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0.im, particularly 0.1 and 0.5.im, and have a pH in the range of 5.5 to 8.0.

The emulsion compositions can be those prepared by mixing an anti-canine VEGF antibody with INTRALIPID™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

To practice the method disclosed herein, an effective amount of the pharmaceutical composition noted above can be administered to a canine subject (e.g., a dog having, suspected of having, or at risk for an angiogenesis-related disorder such as cancer) in need of the treatment via a suitable route. A canine subject that needs the treatment may be a canine having, at risk for, or suspected of having an angiogenesis-related disease, as described herein. A canine subject having an angiogenesis-related disease can be identified by routine medical examination. A canine subject suspected of having an angiogenesis-related disease may show one or more symptoms of the disease. Such subjects can also be identified via routine medical examination. A canine subject at risk for an angiogenesis-related disease such as cancer can be a subject having one or more of the risk factors for that disease.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual dog parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. For example, antibodies that are compatible with the canine immune system, such as caninized antibodies or fully canine antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or reduction of cell proliferation. Alternatively, sustained continuous release formulations of anti-canine VEGF antibodies may be appropriate. Various formulations and devices for achieving sustained release are known in the art.

In one example, dosages for an anti-canine VEGF antibody may be determined empirically in canines that have been given one or more administration(s) of anti-canine VEGF antibodies. Canine subjects are given incremental dosages of the antibodies. To assess efficacy of the antibodies, an indicator of the angiogenesis-related disease (such as cell proliferation) can be followed.

Generally, for administration of any of the antibodies described herein, an initial candidate dosage can be about 2 mg/kg. For the purpose of the present disclosure, a typical daily dosage might range from about any of 0.1 μg/kg to 3 μg/kg to 30 μg/kg to 300 μg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate an angiogenesis-related disease (e.g., cancer) or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 μg/mg to about 2 mg/kg (such as about 3 μg/mg, about 10 μg/mg, about 30 μg/mg, about 100 μg/mg, about 300 μg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

For the purpose of the present disclosure, the appropriate dosage of an anti-canine VEGF antibody will depend on the specific antibody (or compositions thereof) employed, the type and severity of the allergic airway disorder to be treated, whether the antibody is administered for preventive or therapeutic purposes, previous therapy, the canine subject's clinical history and response to the antibody, and the discretion of the attending veterinarian. Typically the veterinarian will administer an anti-canine VEGF antibody until a dosage is reached that achieves the desired result. Administration of an antibody can be continuous or intermittent, depending, for example, upon the subject's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing an angiogenesis-related disorder.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In some embodiments, an anti-canine VEGF antibody is administered via site-specific or targeted local delivery techniques, e.g., delivered to the airway of a canine subject. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

It is also apparent that an expression vector can be used to direct expression of any of the antibodies described herein (e.g., anti-canine VEGF antibody). The therapeutic antibodies described herein can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, *Hum. Gene Ther*. (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther*. (1992) 3:147); ligand-linked DNA (see, e.g., Wu, *J. Biol. Chem*. (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, *Mol. Cell. Biol*. (1994) 14:2411, and in Woffendin, *Proc. Nall. Acad. Sci*. (1994) 91:1581.

The particular dosage regimen, i.e., dose, timing and repetition, used in the methods described herein will depend on the particular canine subject and that subject's medical history.

Kits for Use in Treating Angiogenesis-Related Disorders

The present disclosure also provides kits for use in treating angiogenesis-related disorders in dogs, such as proliferative disorders (e.g., cancer). Such kits can include one or more containers comprising any of the anti-canine VEGF antibodies as described herein, e,g, mAb 57C, a functional equivalent thereof, or a functional variant thereof as described herein In some embodiments, the kit can comprise instructions for use in accordance with any of the methods described herein. The included instructions can comprise a description of administration of the antibody to treat, delay the onset, or alleviate a disease associated with abnormal angiogenesis according to any of the methods described herein. The kit may further comprise a description of selecting an individual dog suitable for treatment based on identifying whether that individual has the target disease. In still other embodiments, the instructions comprise a description of administering an anti-canine VEGF antibody to an individual at risk of the disease.

The instructions relating to the use of an anti-canine VEGF antibody as described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating an angiogenesis-related disorder such as cancer. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-canine VEGF antibody as described herein. The kit may further comprise an additional chemotherapeutic agent suitable for treat cancer in dogs.

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: Development of Antibodies Binding to Dog VEGF

Mammalian and *E. coli* cells were engineered to express recombinant a canine VEGF protein. The recombinant protein produced in the mammalian and *E. coli* host cells were purified. The mammalian cell-produced VEGF was used as an antigen to immunize mice. Spleens from the mice producing anti-canine VEGF antibodies were collected and fused with a myeloma cell line using standard techniques. The fused hybridoma cells were screened twice using ELISA to identify positive clones. The mammalian cell-produced VEGF was used in the first round of screening, and the *E. coli*-produced VEGF was used in the second round of screening to identify hybridoma clones that recognized the peptide sequence of VEGF rather than the carbohydrate moieties that may be present on VEGF protein produced in mammalian cells.

The hybridoma clones positive for the production of anti-canine VEGF antibodies were inoculated into mice for ascite production. Antibodies were purified from the mouse ascite fluid and tested for the ability to inhibit proliferation of human endothelial cells HUVEC. Antibody mAb 57C was selected because it resulted in a significant inhibition of proliferation of HUVEC cells. The in vivo biological function of antibody 57C was also assessed. Antibody 57C was able to inhibit dog breast tumor proliferation as well as reduce the presence of the CD31 endothelial cell marker in a xenograft animal model for dog cancer.

RNA was isolated from hybridoma cells expressing the anti-canine VEGF antibody 57C. Five μg of total RNA from the cells was used to amplify the 5' end of the 57C monoclonal antibody mRNA using the Gene Racer kit (Invitrogen). The amplified fragment was gel purified using the QIAquick Spin kit (Qiagen) and cloned into pCR-TOPO vector using the TOPO TA Cloning kit (Invitrogen). The cloned fragment was sequenced to obtain the nucleic acid sequence data of the heavy chain and light chain. Based on the sequencing results, primers specific to the anti-canine VEGF antibody 57C were used to amplify the heavy chain and light chain from the hybridoma cDNA, which resulted in identical sequences as previously obtained, further confirming the accuracy of the nucleic acid sequences.

Example 2: Effect of Anti-Canine VEGF mAb 57C in Reducing Tumor Size and Volume

Figure 1A:
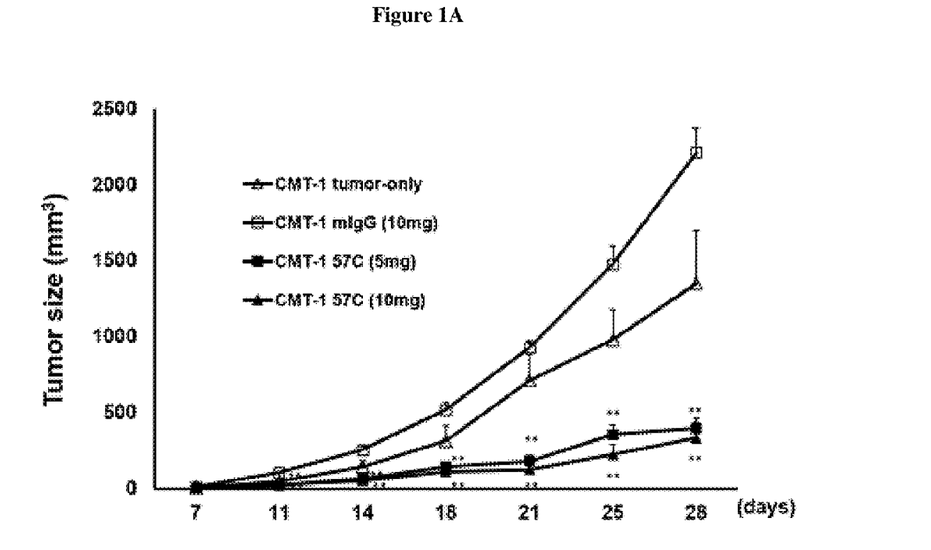
FIG. 1A shows tumor size at various times following administration of mIgG, anti-canine VEGF mAb 57C, no treatment (CMT-1 tumor only).
Figure 1B:
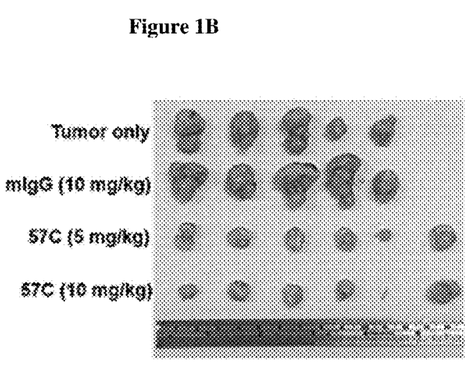
FIG. 1B shows tumors obtained from mice following the indicated treatment.
Figure 1C:
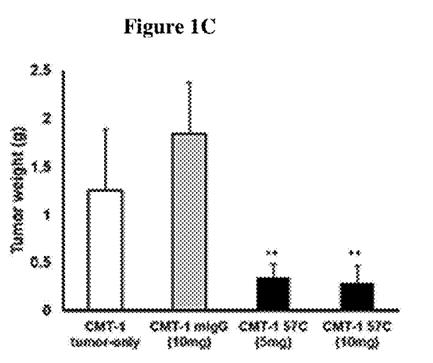
FIG. 1C shows a graph of the tumor volume as measured using a vernier caliper. ** represents P<0.01 as compared to mIgG controls.

Eight-weeks-old female NOD/SCID mice were used in the experiments described herein. Each mouse was subcutaneously (s.c.) injected with canine mammary tumor cells (CMT-1 cells) ($1 \times 10^6$ cells/mouse) in the left mammary fat pad. To mimic application to a canine after surgery and assess the effect of the antibody on the growth of residual tumor cells on the primary site, the mice were administered antibodies one day after injection of the CMT-1 cells. Mice were randomly assigned to four groups and subcutaneously administered mouse IgG (mIgG; 10 mg/kg (n=5)) or the anti-canine VEGF antibody 57C at two different dosages (5 mg/kg (n=6) or 10 mg/kg (n=6)) three times per week or received no treatment (CMT-1 tumor only (n=5)) for the duration of the experiment. The mice were sacrificed 30 days after the initial CMT-1 injection, and the tumors were collected and weighed. As demonstrated in FIGS. 1A-1C, mice that received either dosage of the anti-canine VEGF antibody 57C had reduced tumor size compared to mice that received mIgG or no treatment.

Figure 2A:
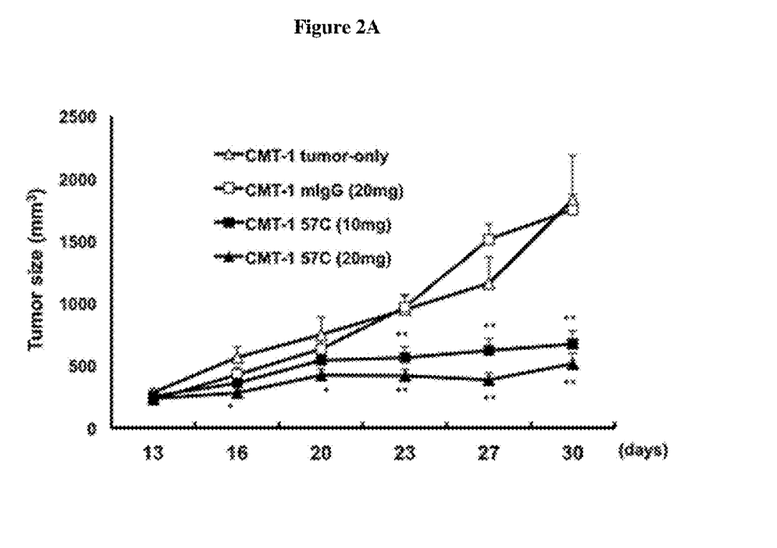
FIG. 2A shows tumor size at various times following administration of mIgG, anti-canine VEGF mAb 57C, or no treatment (CMT-1 tumor only).
Figure 2B:
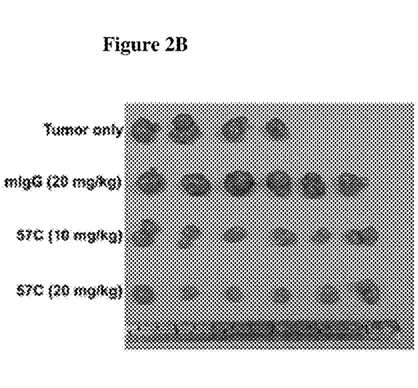
FIG. 2B shows tumors obtained from mice following the indicated treatment.
Figure 2C:
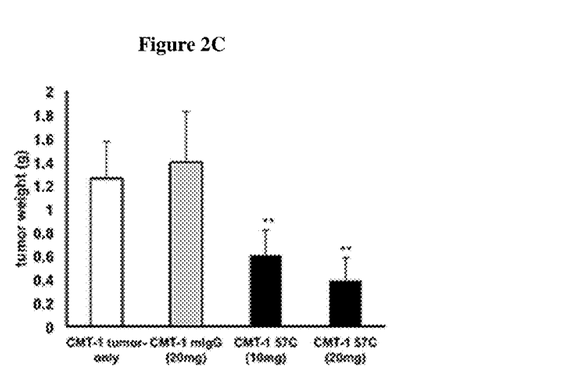
FIG. 2C shows a graph of the tumor volume as measured using a vernier caliper. * represents P<0.05 as compared to mIgG controls; ** represents P<0.01 as compared to mIgG controls.

In the second experiment, 8-week-old female NOD/SCID mice were subcutaneously (s.c.) injected with CMT-1 cells (1×10⁶ cells/mouse) in the left mammary fat pad. To assess the effect of the antibodies on tumors already formed, the injected CMT-1 cells were allowed to grow for 13 days after which the mice were subcutaneously administered mIgG (20 mg/kg; n=6), or anti-canine VEGF antibody 57C at two different dosages (10 mg/kg (n=6); 20 mg/kg (n=6)) twice per week or received no treatment (CMT-1 tumor only) for the duration of experiment. The mice were sacrificed 30 days after the initial CMT-1 injection, and the tumors were collected and weighed. As demonstrated in FIGS. 2A-2C, mice that received either dosage of the anti-canine VEGF antibody 57C had reduced tumor size compared to mice that received mIgG or no treatment, suggesting that the anti-canine VEGF antibody 57C may be combined with a chemotherapeutic agent to kill cancers cells in a tumor mass.

Figure 3A:
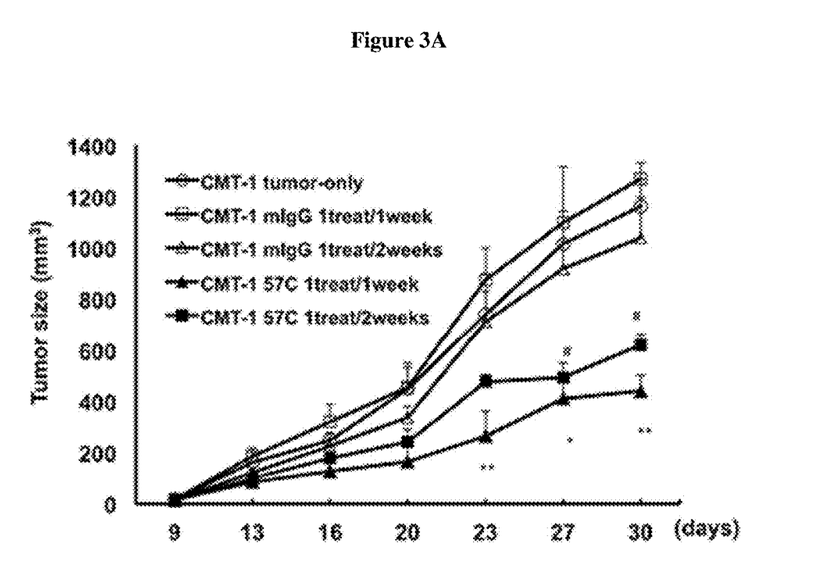
FIG. 3A shows tumor size at various times following administration of mIgG, anti-canine VEGF mAb 57C, or no treatment (CMT-1 tumor only).
Figure 3B:
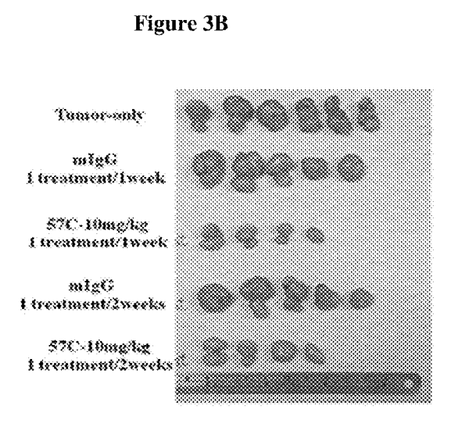
FIG. 3B shows tumors obtained from mice following the indicated treatment.
Figure 3C:
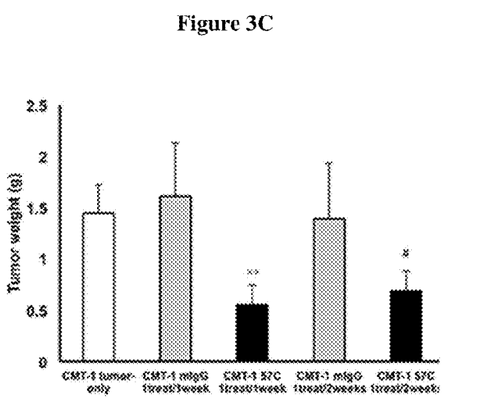
FIG. 3C shows a graph of the tumor volume as measured using a vernier caliper. ** represents P<0.01 compared with mIgG controls; # represents P<0.05 as compared to mIgG controls (one time per two weeks).

In the third experiment, 8-week-old female NOD/SCID mice were subcutaneously (s.c.) injected with CMT-1 cells (1×10⁶ cells/mouse) in the left mammary fat pad. The following day, mice were subcutaneously administered mIgG (10 mg/kg (n=5)) once per week, mIgG (10 mg/kg; (n=5)) once per two weeks, the anti-canine VEGF antibody 57C (10 mg/kg (n=5)) once per week, the anti-canine VEGF antibody 57C (10 mg/kg (n=5)) once per two weeks, or received no treatment (CMT-1 tumor only). The mice were sacrificed 35 days after the initial CMT-1 injection, and the tumors were collected and weighed. As demonstrated in FIGS. 3A-3C, mice that received the anti-canine VEGF antibody 57C either once per week or once per two weeks had reduced tumor size compared to mice that received mIgG or no treatment.

REFERENCES

1. Pavlidis, E. T. & Pavlidis, T. E. Role of bevacizumab in colorectal cancer growth and its adverse effects: a review. *World journal of gastroenterology: WJG* 19, 5051-5060 (2013).
2. Trevisan, E., et al. Antiangiogenic therapy of brain tumors: the role of bevacizumab. *Neurological sciences: official journal of the Italian Neurological Society and of the Italian Society of Clinical Neurophysiology* 35, 507-514 (2014).
3. Keating, G. M. Bevacizumab: a review of its use in advanced cancer. *Drugs* 74, 1891-1925 (2014).
4. Vail, D. M. & MacEwen, E. G. Spontaneously occurring tumors of companion animals as models for human cancer. *Cancer investigation* 18, 781-792 (2000).
5. MacEwen, E. G. Spontaneous tumors in dogs and cats: models for the study of cancer biology and treatment. *Cancer metastasis reviews* 9, 125-136 (1990).
6. Gamlem, H., Nordstoga, K. & Glattre, E. Canine neoplasia—introductory paper. *APMIS. Supplementum*, 5-18 (2008).
7. Tien, Y. T., et al. Downregulation of the KLF4 transcription factor inhibits the proliferation and migration of canine mammary tumor cells. *Veterinary journal* (2015).
8. Sleeckx, N., de Rooster, H., Veldhuis Kroeze, E. J., Van Ginneken, C. & Van Brantegem, L. Canine mammary tumours, an overview. *Reproduction in domestic animals=Zuchthygiene* 46, 1112-1131 (2011).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An isolated antibody that binds a canine vascular endothelial growth factor (VEGF), wherein the antibody comprises
   (i) a heavy chain that includes a heavy chain complementarity determining region 1 (HC CDR1) set forth as SEQ ID NO: 5, a heavy chain complementarity determining region 2 (HC CDR2) set forth as SEQ ID NO: 6, and a heavy chain complementarity determining region 3 (HC CDR3) set forth as SEQ ID NO: 7, and
   (ii) a light chain that includes a light chain complementarity determining region 1 (LC CDR1) set forth as SEQ ID NO: 8, a light chain complementarity determining region 2 (LC CDR2) set forth as SEQ ID NO: 9, and a light chain complementarity determining region 3 (LC CDR3) set forth as SEQ ID NO: 10.

2. The isolated antibody of claim 1, wherein the heavy chain comprises a heavy chain variable region that comprises the amino acid sequence of SEQ ID NO: 2.

3. The isolated antibody of claim 2, wherein the light chain comprises a light chain variable region that comprises the amino acid sequence of SEQ ID NO: 4.

4. The isolated antibody of claim 1, wherein the light chain comprises a light chain variable region that comprises the amino acid sequence of SEQ ID NO: 4.

5. The isolated antibody of claim 1, wherein the antibody is a full length antibody or an antigen-binding fragment thereof.

6. The isolated antibody of claim 1, wherein the antibody is a canine antibody or a caninized antibody.

7. A pharmaceutical composition comprising the antibody of claim 1 and a pharmaceutically acceptable carrier.

8. A method for inhibiting VEGF in a canine subject, comprising administering to a canine subject in need thereof an effective amount of an antibody of claim 1.

9. The method of claim 8, wherein the antibody comprises a heavy chain variable region comprising the amino acid sequence of SEQ ID NO: 2, and a light chain variable region comprising the amino acid sequence of SEQ ID NO: 4.

10. The method of claim 8, wherein the antibody is a full length antibody or an antigen-binding fragment thereof.

11. The method of claim 8, wherein the canine subject has or is suspected of having an angiogenesis-related disease.

12. The method of claim 11, wherein the canine subject has an angiogenesis-related disease is selected from the group consisting of a proliferative disease, macular degeneration, age-related macular degeneration, diabetic retinopathy, retinal detachment, glaucoma, pterygium of the conjunctiva and cornea, neuomyelitis optica, corneal neovascularization, neoplastic meningitis, myelofibrosis, radiation necrosis, and keloid.

13. The method of claim 11, wherein the angiogenesis-related disease is cancer.

14. The method of claim 13, wherein the cancer is selected from the group consisting of glioblastoma, sarcoma, hepatocellular carcinoma, inflammatory breast carcinoma pancreatic cancer, metastatic melanoma, ovarian cancer, high-risk neuroblastoma, esophageal cancer, gastric cancer, metastatic head tumor, metastatic neck tumor, cervical cancer, peritoneal cancer, and squamous cell carcinoma.

15. The method of claim 13, further comprising administering to the canine subject a chemotherapeutic agent.

* * * * *